United States Patent
Vija et al.

(10) Patent No.: US 11,497,461 B1
(45) Date of Patent: Nov. 15, 2022

(54) SOLID-STATE DOSE CALIBRATION SYSTEM

(71) Applicant: Siemens Medical Solutions USA, Inc., Malvern, PA (US)

(72) Inventors: Alexander Hans Vija, Evanston, IL (US); Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 6 days.

(21) Appl. No.: 17/302,425

(22) Filed: May 3, 2021

(51) Int. Cl.
*A61B 6/00* (2006.01)
*A61B 6/03* (2006.01)

(52) U.S. Cl.
CPC .............. *A61B 6/582* (2013.01); *A61B 6/037* (2013.01); *A61B 6/4266* (2013.01)

(58) Field of Classification Search
CPC ........ A61B 6/582; A61B 6/037; A61B 6/4266
See application file for complete search history.

(56) References Cited

U.S. PATENT DOCUMENTS

| | | |
|---|---|---|
| 11,191,515 B1 | 12/2021 | Vija et al. |
| 2005/0213705 A1 * | 9/2005 | Hoffman ............... G01T 1/1642 378/4 |
| 2012/0061581 A1 * | 3/2012 | Hugg ................ G21K 1/02 250/394 |
| 2018/0020535 A1 * | 1/2018 | Cooley ................ A61N 5/1065 |
| 2020/0367839 A1 * | 11/2020 | Iniewski .......... G01N 23/20066 |
| 2022/0076808 A1 | 3/2022 | Vija et al. |

FOREIGN PATENT DOCUMENTS

| | | |
|---|---|---|
| KR | 20170000652 A | 1/2017 |
| WO | 2022055539 A1 | 3/2022 |

OTHER PUBLICATIONS

P. Zanzonico, "Routine quality control of clinical nuclear medicine instrumentation: a brief review", the Journal of Nuclear Medicine, vol. 49, No. 7, pp. 1114-1131. (Year: 2008).*

* cited by examiner

*Primary Examiner* — Kiho Kim

(57) ABSTRACT

Systems and methods for dose calibration. A dose calibrator may include one or more radiation sources, one or more solid-state detectors and one or more plates positioned between the one or more radiation sources and the one or more solid-state detectors. The one or more solid-state detectors capture one or more images based on emissions received from the one or more radiation sources through the one or more plates for estimating activity of the one or more radiation sources.

20 Claims, 5 Drawing Sheets

200

SOLID-STATE DOSE CALIBRATION SYSTEM

TECHNICAL FIELD

The present disclosure generally relates to medical imaging, and more particularly to solid-state dose calibration system for functional imaging.

BACKGROUND

Functional imaging is a medical imaging technique for detecting or measuring changes in metabolism, blood flow, regional chemical composition and absorption. Positron emission tomography (PET) and single photon emission computed tomography (SPECT) are two types of functional imaging. Functional imaging uses a radioisotope or radiotracer to determine physiological activity within a patient. The emissions from the radiotracer are detected in the functional image data. The activity concentration (i.e., the concentration of the radiotracer from different locations) is reconstructed from the detected emissions.

The error in the dose of radiotracer applied to the patient introduces a source of error in quantitative functional imaging. A dose value is provided using a measurement by a dose calibrator. A standard benchtop dose calibrator typically contains an ionization chamber, a high voltage power supply, an electronic amplifier and a display unit on which one can select the radiotracer to be calibrated. The ionization chamber is used to measure the total amount of ionization produced by the sample to be calibrated. The ionization chamber is typically a hermetically sealed chamber that contains Argon gas under high pressure and two electrodes having an electric potential between them. When the vial or syringe containing the radiotracer is placed into the ionization chamber, the Argon gas is ionized. Counts of emissions from the radiotracer are detected. The activity concentration of the radiotracer from different locations is reconstructed from the detected emissions. The activity of the radiotracer may then be determined by looking up a table or database using the detected counts of emission. The output activity is typically displayed on the display unit in either millicurie (mCi) or megabecquerel (MBq).

Such standard benchtop dose calibrators operate based on detection of emission counts of pre-defined sources of radiotracer. For example, an internal look-up table (LUT) with predefined settings for corresponding radioisotopes is pre-loaded into the dose calibrator. The user is responsible to manually select, via the display unit, which radioisotope is being read out. The LUT is used to correct for the measurements, assuming the pre-loaded isotope is exactly the same as the one being measured (e.g., no cocktails, no contamination). The pre-defined mapping relationship between the counts and activity levels is non-linear, thereby giving rise to another source of inaccuracy. The ionization chamber is limited in terms of spectroscopic performance. Current dose calibrators are not intended to automatically measure single sources and/or cocktails of sources with the degree of accuracy required for dosimetry applications in SPECT.

Cross calibration techniques have been proposed to mitigate current dose calibrator deficiencies. However, such techniques are complicated and add additional burden to existing SPECT workflows. Additionally, specialized collimators need to be acquired and expensive cross-calibration sources need to be maintained at the hospitals.

SUMMARY

Described herein are systems and methods for dose calibration. A dose calibrator may include one or more radiation sources, one or more solid-state detectors and one or more plates positioned between the one or more radiation sources and the one or more solid-state detectors. The one or more solid-state detectors capture one or more images based on emissions received from the one or more radiation sources through the one or more plates for estimating activity of the one or more radiation sources.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
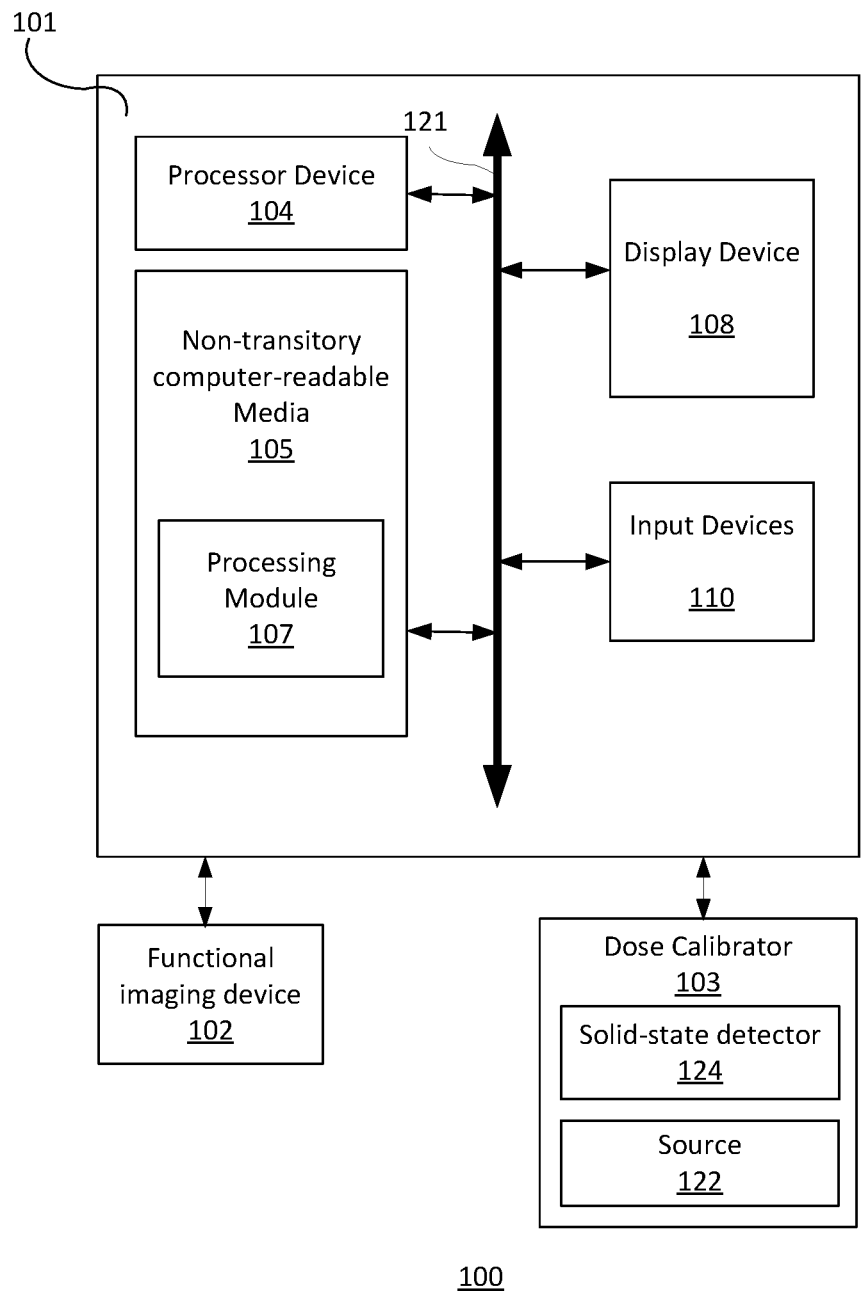
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI (magnetic resonance imaging), PET (positron emission tomography), PET-CT (computed tomography), SPECT (single photon emission computed tomography), SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images, voxels for 3D images, doxels for 4D datasets). The image may be, for example, a medical image of a subject collected by CT (computed tomography), MM (magnetic resonance imaging), ultrasound, or any other medical imaging system known to one of ordinary skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture, 3D volume or 4D dataset. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, "voxels" for volume image elements, often used with respect to 3D imaging, and "doxels" for 4D datasets can be used interchangeably. It should be noted that the 3D volume image is itself synthesized from images obtained as pixels on a 2D sensor array and displays as a 2D image from some angle of view. Thus, 2D image processing and image analysis techniques can be applied to the 3D volume images. In the description that follows, techniques described as operating upon doxels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel", "subject voxel" and "subject doxel" are used to indicate a particular image element as it is operated upon using techniques described herein.

One aspect of the present framework is a dose calibrator that includes one or more solid-state detectors. The one or more solid-state detectors capture one or more images based on emissions received from one or more radiation sources through one or more plates. The one or more images are used to determine activity of the one or more radiation sources. The one or more plates may include, for example, rotatable or translatable disks with multiple pinholes distributed therein. One or more system parameters, such as sizes and/or number of pinholes, source to plate distance and/or detector to plate distance, may be automatically adapted to measure a broad range of photon energies and source activity levels, thereby enhancing user-friendliness. The present dose calibrator may also automatically identify the one or more radiation sources being measured, thereby advantageously eliminating the need to manually identify the one or more radiation sources and pre-load a look-up table.

Advantageously, the acquisition time of the present dose calibrator is very short (e.g., less than 10 seconds). Unlike conventional dose calibrators that derive activity of pre-defined radiation sources based on detected counts of emission, the present dose calibrator directly measures activity from images captured by the one or more solid-state detectors at room temperature. Such solid-state detectors advantageously avoid the inaccuracy introduced by non-linear conversion of counts to activity.

The present dose calibrator has a compact size and weight that enable it to be a benchtop and/or modular system. Due to the minimized weight and size, the dose calibrator is capable of being deployed in hospitals, thereby reducing the need to maintain cross-calibration sources at the sites and enhancing the user-friendliness of the workflow without complicated cross-calibration procedures.

The present dose calibrator advantageously detects emissions at a wide range of low to high photon energies (e.g., 100 keV to 3 MeV). The dose calibrator may detect emissions at energies beyond 511 keV. Additionally, a broad range of low to high source activities varying from the µCi range through the Ci range may be measured. The activity range may be around $10^6$ for performing both wipe test and activity measurements in a single dose calibrator. The use of solid-state detectors enhances the usability of dosimetry tools provided by functional imagers (e.g., SPECT). A national institute of standards and technology (NIST) traceable source(s) and/or NIST traceable dosimetry kernels may be provided for any of various types of isotope compounds or mixtures in different form factors of containers (e.g., syringe or vial). These and other exemplary features and advantages will be described in more details herein.

FIG. 1 is a block diagram illustrating an exemplary system 100. The system 100 includes a computer system 101, a functional imaging device 102 and a dose calibrator 103. Computer system 101 may be separate or part of the functional imaging device 102 or the dose calibrator 103. For example, computer system 101 may be a desktop personal computer, a portable laptop computer, another portable device, a mini-computer, a mainframe computer, a server, a cloud infrastructure, a storage system, a dedicated digital appliance, a communication device, or another device having a storage sub-system configured to store a collection of digital data items. Additional, different, or fewer components may be provided. For example, the system 100 is a computer without the functional imaging device 102.

Computer system 101 may include a processor device or central processing unit (CPU) 104 coupled to one or more non-transitory computer-readable media 105 (e.g., computer storage or memory), a display device 108 (e.g., monitor) and various input devices 110 (e.g., mouse, touchscreen, keyboard) via an input-output interface 121. Computer system 101 may further include support circuits such as a cache, a power supply, clock circuits and a communications bus.

Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 105. In particular, the present techniques may be implemented by a processing module 107. Non-transitory computer-readable media 105 may include random access memory (RAM), read-only memory (ROM), magnetic floppy disk, flash memory, and other types of memories, or a combination thereof. The computer-readable program code is executed by processor device 104 to process images acquired by, for example, a functional imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing image sets, patient records, knowledge base, and so forth. Such data may also be stored in external storage or other memories. The external storage may be implemented using a database management system (DBMS) managed by the processor device 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The functional imaging device 102 is a radiological imaging device that acquires medical image data by using a radioisotope or radiotracer to determine physiological activity within a patient. Such functional imaging device 102 may use technologies of positron emission tomography (PET), single-photon emission computed tomography (SPECT), or a combination thereof. For imaging uptake or activity concentration in a patient, the functional imaging device 102 detects emissions of a dose of radiotracer from the patient. The emissions occur from any location in a finite source (i.e., the patient). The radiotracer in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic processes. The functional imaging device 102, using the processor device 104 or another processor, is configured to reconstruct the imaged volume by applying a system matrix to the detected data.

The dose calibrator 103 is external to the functional imaging device 102. The dose calibrator 103 includes one or more solid-state detectors 124 for detecting activity of a dose of radiotracer. The dose calibrator 103 is shown connected to computer system 101, but may instead have its own processor or connect to a computer with another processor. The radiation source 122 may be in the form of a point source positioned in the dose calibrator 103. The radiation source 122 is formed from one or more radioisotopes to emit at different energies or with different energy peaks. A cocktail (or mix) of different radioisotopes and/or a radioisotope that emits at multiple energies may be used.

The emissions from the radiation source 122 are captured by one or more images generated by one or more solid-state detectors 124. The one or more images from the dose calibrator 103 are received by processing module 107. Processing module 107 estimates the activity of the source 122 based on the one or more images.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
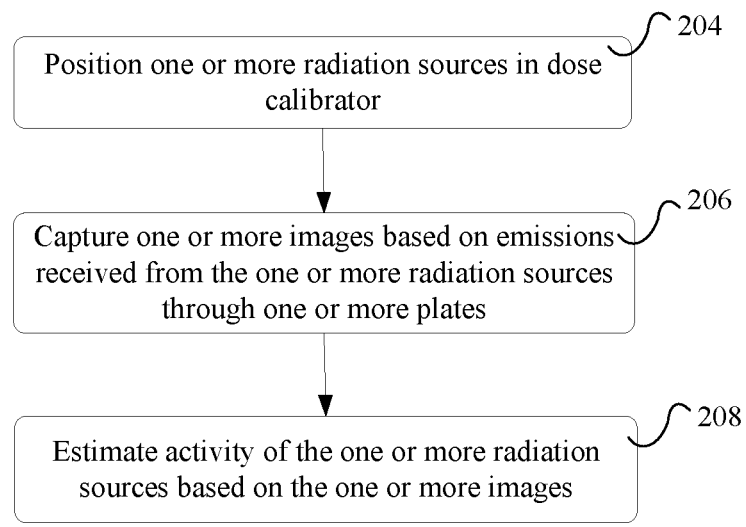
FIG. 2 shows an exemplary dose calibration method.

FIG. 2 shows an exemplary dose calibration method 200. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 204, one or more radiation (or radioisotope) sources 122 are positioned in the dose calibrator 103. A radiation source 122 may be packaged in a container, such as a glass, metal or plastic vial, syringe or other housing of any given size and shape, and positioned within the dose calibrator 103. The container type may be manually selected or automatically detected by processing module 107. It should be appreciated that a cocktail of multiple radiation sources 122 may also be positioned in the dose calibrator 103.

Figure 3A:
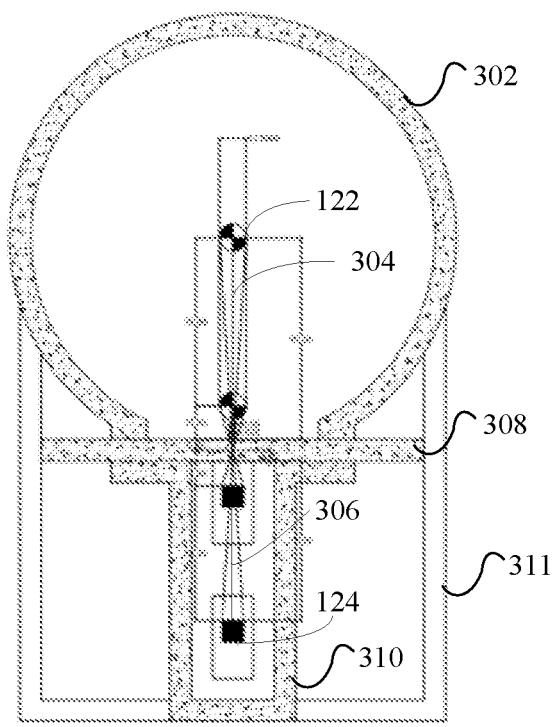
FIG. 3a shows a top-view of an exemplary dose calibrator.

FIG. 3a shows a top-view of an exemplary dose calibrator 103. Dose calibrator 103 includes a radiation source 122, solid-state detector 124 and a plate 308 positioned between the radiation source 122 and solid-state detector 124. Dose calibrator 103 may be sized to be carried or moved around. In some implementations, dose calibrator 103 is sized to be compact, portable and/or placed on a benchtop. The height may be between 10 cm to 50 cm, the width may be between 10 cm to 50 cm, and the depth may be between 10 cm to 50 cm. For example, the dimensions of the dose calibrator 103 may be 25 cm (height) by 25 cm (width) by 50 cm (depth). The weight of the dose calibrator 103 varies depending on the plate size and shielding needed. The weight may range from 15 lbs. (~7.5 kg) up to 40 lbs. (~20.0 kg). Any other dimensions, weights and/or sizes may be provided. Dose calibrator 103 may further be broken down into sub-systems to increase portability.

In some implementations, radiation source 122 is positioned within a first housing 302. Radiation source 122 may be placed into a cavity (e.g., dome) formed by the first housing 302 through an opening. First housing 302 serves as a radiation shield and provides mechanical protection for the radiation source 122. First housing 302 may be made of, for example, steel, lead, tungsten, alloys thereof or a combination thereof. A holder, such as a plastic holder, may be provided to position the radiation source 122. Radiation source 122 may be translatable along the axis 304. Additionally, radiation source 122 may be rotatable around axis 304. More than one axis of rotation and/or translation may also be provided. Solid-state detector 124 is positioned within a second housing 310. Second housing 310 may serve as a radiation shield, as well as provide mechanical protection for solid-state detector 124. Solid-state detector 124 may be translatable along axis 306. Axes 304 and 306 may be parallel and co-linear. More than one solid-state detectors 124, such as two, four or more solid-state detectors 124, may also be provided.

Plate 308 is positioned within a third housing 311 that may serve as mechanical protection for the plate 308. Plate 308 serves as a collimator for controlling or limiting the radioactive energy emitted by radiation source 122 and incident on the solid-state detector 124. In some implementations, plate 308 is rotatable about axis 304. Alternatively, plate 308 may also be translatable in a direction perpendicular to axis 304. Additionally, plate 308 is removable and may be replaced by another plate.

Figure 3B:
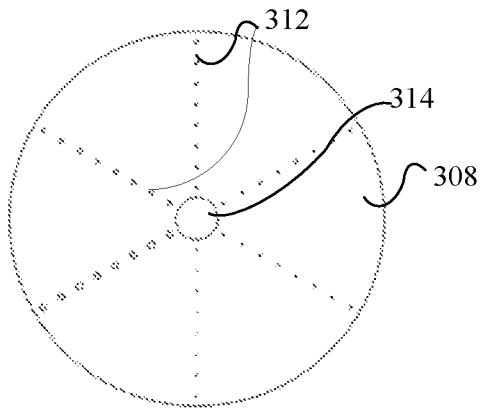
FIG. 3b shows a front view of an exemplary plate.

FIG. 3b shows a front view of an exemplary plate 308. Plate 308 is a rotatable disk with multiple pinholes (or apertures) 312. Pinholes 312 may be distributed on the plate 308 in any configuration. In this example, 6 lines of pinholes with different sizes extend radially from a center hole 314. Each line may include 8 pinholes 312. Other configurations, such as 16 pinholes for each line or multiple adjacent lines (e.g., 2 adjacent lines), may also be provided. Center hole 314 may receive a support shaft for rotating the plate 308 about the axis 304. The lines may also be provided in a non-radial configuration (e.g., rectangular matrix of lines of pinholes) for translatable plates. The sizes and/or number of pinholes 312 may be different for each line. This allows the sizes and/or number of pinholes to be adjusted on-the-fly to compensate for source activity and readout time by rotating or translating the plate 308.

Plate 308 may be made using, for example, tungsten, lead, or a combination thereof. Other materials are also useful. Different materials may be suitable for different energy-level radiation sources. For low energy (e.g., less than 364 keV) radiation sources, the thinnest and therefore most cost-efficient materials may be tungsten or lead. For high energy (e.g., greater than 511 keV) radiation sources, the thinnest and most cost-efficient material is tungsten. A more economical hybrid material (e.g., tungsten powder core) may also be used. The thickness of the plate 308 may be, for example, 2 to 10 mm.

Solid-state detector 124 captures one or more images based on emissions received from the radiation source through the plate 308 for measuring activity of the radiation source 122. Solid-state detector 124 is made up of many individual detector elements, wherein each detector element is isolated from one another. Solid-state detector 124 may be of any size based on weight and space limitations of dose calibrator 103. Solid-state detector 124 may be, for example, 10×10 cm, 5×5 cm, 3×5 cm or 5×7 cm, but other sizes may be used.

Solid-state detector 124 operates at room temperature, configured as a single-pixel or a multi-pixel detector. The material used to make solid-state detector 124 may include a semiconductor, such as cadmium zinc telluride (CZT), cadmium telluride (CdTe), thallium bromide (TlBr) or combination thereof. A higher number of solid-state detectors may be required for measuring with higher sensitivity or activity range. Solid-state detector 124 may be created with wafer fabrication at any thickness, such as 3 mm to 25 mm for CZT detectors. Other thicknesses may also be provided, depending on the material used.

Solid-state detector 124 may include a semiconductor sensor coupled to an application specific integrated circuit (ASIC) to sense low-level signals generated by the semiconductor sensor. The semiconductor sensor may generate the signals by directly converting energy deposited on the semiconductor sensor into electron-hole induced charges or electrical signals. The inputs of the ASIC may be collocated as closely as possible to the pixels of semiconductor sensor to minimize noise in the signals generated by the semiconductor sensor. The ASIC is of any thickness (e.g., less than 1 mm). A plurality of ASICs may be provided, such as 9 ASICS in a 3×3 grid of solid-state detector 124.

Solid-state detector 124 may detect emissions in a wide range of different energies. For example, solid-state detector 124 may detect emissions from radiation source 122 at energies between 100 keV and 3 MeV. Solid-state detector 124 may also be designed to detect emissions at energies in a specific energy range, such as energies beyond 511 keV. Solid-state detector 124 may be used to measure emissions of gamma particles from a radiotracer source. Solid-state detector 124 may also be used to measure alpha particles and/or beta particles, either directly or indirectly, from alpha emitters for instance.

Figure 4:
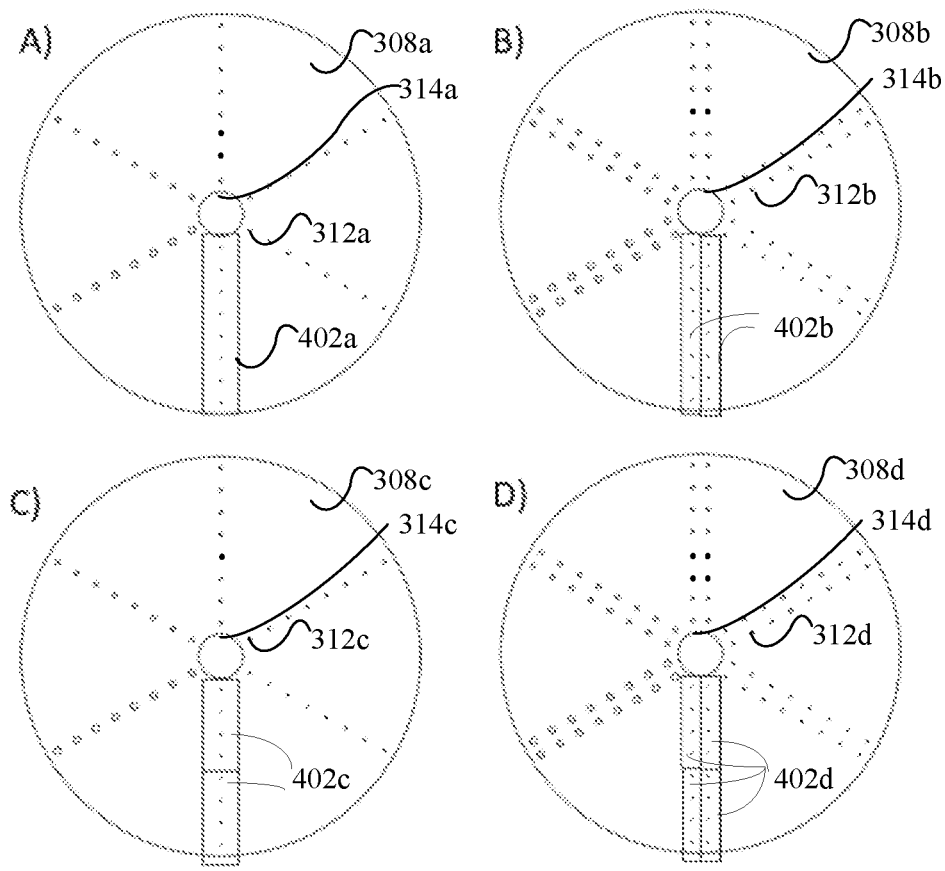
FIG. 4 shows different exemplary plates used for different numbers of solid-state detectors.

FIG. 4 shows different exemplary plates 308a-d used for different numbers of solid-state detectors 124. Plate 308a includes multiple pinholes 312a configured for a single solid-state detector 124. The single solid-state detector 124 is positioned to capture an image of region 402a. Plates 308b-c include pinholes 312b-c configured for two solid-state detectors 124. For plate 308b, the two solid-state detectors 124 are positioned in a single row configuration to capture images of regions 402b. Double adjacent lines of pinholes 312b extending from the center hole 314b of the plate 308b are provided to accommodate the rows of two detectors 124. For plate 308c, the two solid-state detectors 124 are positioned in a single column configuration to capture images of regions 402c. Single lines of pinholes 312c extend from the center hole 314c of the plate 308c. Plate 308d includes pinholes 312d configured for four solid-state detectors 124. The four solid-state detectors 124 are positioned in a double rows and double columns configuration to capture images of regions 402d. Double lines of pinholes 312d extend from the center hole 314d of the plate 308d to accommodate the four detectors 124. It should be appreciated that other configurations of solid-state detectors 124 and plate 308 are also possible.

Sub-dividing the solid-state detectors 124 into more rows enables wider activity ranges to be measured. For example, plates 308c and 308d may be used to capture images of radiation sources 122 with twice the activity ranges of radiation sources 122 imaged using plates 308a and 308b respectively. Sub-dividing the solid-state detectors 124 into more columns enables higher measurement sensitivities. For example, plates 308b and 308d may be used to capture images with twice the sensitivity of images captured using plates 308a and 308c respectively.

More semiconductor sensors and ASICs may be added within the same area to split the counts into multiple ASICs and readouts, thereby increasing the ability to read hotter radiation sources with less dead time. Dead time refers to the amount of time that the ASIC needs to stop acquisition to read the event information. Dead time occurs due to the fact that acquisition and readout cannot usually be optimally and simultaneously performed within the same ASIC. Adding more ASICs within the same area allows the rest of the sensor to be active while only a fraction is dead during readout, instead of the entire sensor being dead. For example, one sensor may have 32 pixels and each pixel may have a size of 1×1 mm², which can be arranged in an array of 16 mm×2 mm in size to readout at X counts/second. If the pixel size is reduced to 0.5×0.5 mm², 4 ASICs may be used in an array of 32 mm×4 mm to cover the same area (16×2 mm²) The count rate capability may then be increased by a factor of 4.

Figure 5:
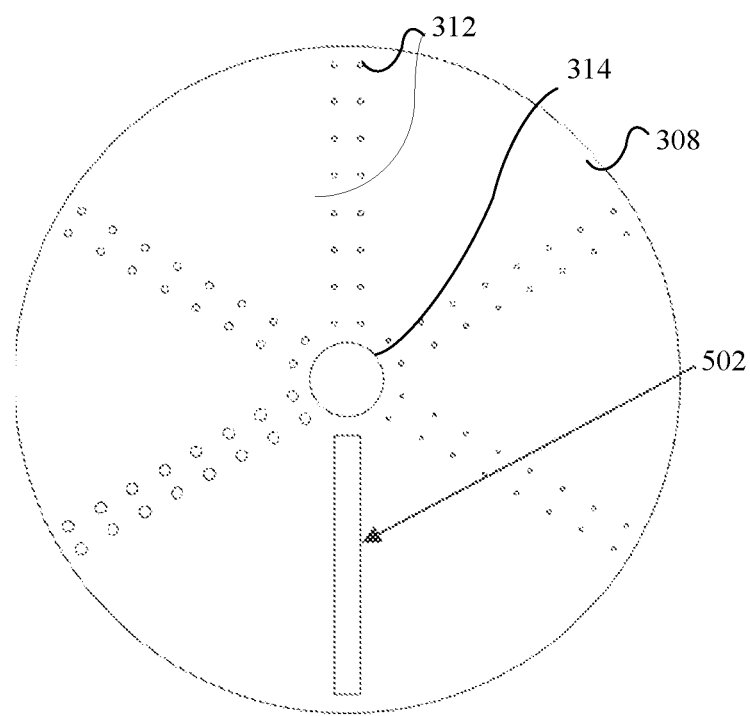
FIG. 5 shows an exemplary plate for radiation sources with high energy emissions.

FIG. 5 shows an exemplary plate 308 for radiation sources 122 with high energy emissions (e.g., more than 600 keV). Plate 308 includes a long slit 502 (instead of collimator pinholes) extending from the center hole 314. The long slit 502 enables image formation to change from physical collimation (i.e., pinholes) to electronic collimation using Compton imaging for higher energies up to, e.g., 3 MeV. Filters may be provided to reduce or limit incident flux.

In some implementations, processing module 107 adaptively controls or adjusts one or more system parameters of the dose calibrator 103 on-the-fly during operation of the dose calibrator 103. The adjustment may be made adaptively based on measured dead-time. The size of the pinholes may be adjusted to accommodate radiation sources with different activity levels. If dead-time is too high, processing module 107 may automatically reduce pinhole size to minimize total acquisition time to less than 1 minute. Similarly, the thickness of the plate may also be adjusted to accommodate radiation sources with different energy levels.

As discussed previously, the plate 308 may include lines of pinholes with different sizes and numbers. The sizes and/or number of pinholes in the plate 308 may be adjusted by rotating or translating the plate 308 to align the desired set of pinholes with the imaging region. Additionally, the thickness may be varied within a plate, so the same plate 308 may be used for low- and high-energies by rotating or translating the plate to align the desired area with the imaging region. For example, half of the plate 308 may have reduced thickness, while the other half has an increased thickness. As another example, the plate 308 may have alternating thicknesses (e.g., thick-thin-thick-thin- . . . ) for all sets of pinhole sizes, or a combination thereof.

Processing module 107 may also adaptively adjust the distance between the radiation source 122 and the plate 308 by moving the radiation source 122 along the translation axis 304. The distance between the radiation source 122 and plate 308 defines the magnification of the source projection on the solid-state detector 124. Processing module 107 may also adaptively adjust the distance between the solid-state detector 124 and the plate 308 by moving the solid-state detector 124 along the translation axis 306. Optimization of these distances minimizes deadtime and increases overall system sensitivity.

In some implementations, dose calibrator 103 is modular. One or more parts of the dose calibrator 103 may be replaced to accommodate radiation sources with different energy levels of interest. In some implementations, the shield (e.g., first housing 302, second housing 310) may be replaced with a thicker shield to measure a higher energy radiation source 122. Plate 308 may also be replaced with a plate of different thickness for a radiation source with a different energy level.

Returning to FIG. 2, at 206, one or more images are captured based on emissions received from the one or more radiation sources 122 through one or more plates 308. The one or more radiation sources 122 emit X-rays or gamma-rays characteristic of the radiotracer. Some of these emissions are detected by one or more solid-state detectors 124 to generate the one or more images. Either planar or tomographic three-dimensional images of the radiation source 122 may be acquired. Planar images are two-dimensional images directly captured by the solid-state detector 124. Processing module 107 may reconstruct tomographic three-dimensional images by rotating the radiation source 122 and capturing images of the radiation source 122. The tomographic three-dimensional images provide a more accurate and quantitative representation of activity distribution of the radiation source 122.

At 208, processing module 107 estimates the activity of the one or more radiation sources 122 based on the one or more images. Processing module 107 counts the detected emissions in the one or more images to estimate the activity. See, for example, U.S. patent application Ser. No. 16/949, 298, titled "Internal Dose Assessment with Portable Single Photon Emission Computed Tomography", filed on Oct. 23, 2020, and PCT Patent Application No. PCT/US2020/ 070520, titled "Mini-SPECT as Dosimeter", filed on Sep. 10, 2020, which are all herein incorporated by reference for all purposes. The locations of the emissions (e.g., lines of response) may be recorded. The energy level of the emissions may or may not be recorded. Processing module 107 may determine a broad range of low to high source activities varying from the µCi range through the Ci range by adjusting the one or more parameters (e.g., pinhole sizes, distances) of the dose calibrator 103. The activity range may be around $10^6$ for measuring very weak sources (e.g., µCi activity) for performing wipe test and measuring very hot sources (e.g., Ci activity) in a single dose calibrator.

Processing module 107 may further determine the dose from the measured activity over time. Additionally, dose kernels may be directly measured for dosimetry applications. To determine the dose, a dose model may be fit to the measured activity. This dose model is fit to reconstructed activity or fit in parametric reconstruction from the emissions. Any dose model may be used. The dose model may be a parametric model of pharmaceutical kinetics, such as diffusion, isotope half-life, biological half-life, and/or another characteristic of change over time in dosage being applied from the radiopharmaceutical. Based on fitting, values of the model parameters of the dose model are solved, providing dose for any time and/or total dose for the locations of the distribution.

In some implementations, processing module 107 automatically identifies the isotope or mix of isotopes in the radiation source 122. The isotope may be identified by analyzing the characteristic spectroscopic energy resolution in the one or more images. Machine learning algorithms, such as deep learning techniques, may be used to perform the analysis. Such information need not be manually input, thereby reducing the burden on the operator and enhancing user friendliness.

In some implementations, dose calibrator 103 is calibrated prior to measuring the activity of the radiation source 122 associated with a current patient. Such calibration does not need to occur for each patient and may be performed any other time or periodically (e.g., once or once per week, month or year). Dose calibrator 103 may be calibrated to a standard, such as an NIST traceable calibration source, since the dose calibrator 103 is stable over longer periods of time, and can be used to measure and tomographically image the radiation source provided in containers of different form factors.

To perform the calibration, a standardized, calibrated radiation source 122 may first be placed in the housing 302. The radiation source 122 has a known activity, dose, and/or isotope, such as an NIST source. Dose calibrator 103 detects and measures activity from the radiation source 122. Processing module 107 determines the dose using the measured activity over time. The measured dose is compared with the known dose of the radiation source 122. The difference is used as a weight or a weight is looked up based on the difference, so that the calculated dose from the detected activity is correct (i.e., equal to the known dose of the source). For example, the amplitude and/or distribution represented in the dose model is adjusted. Different calibration techniques may be provided for different geometries and/or isotopes.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A dose calibrator, comprising:
   one or more radiation sources;
   one or more solid-state detectors; and
   one or more plates positioned between the one or more radiation sources and the one or more solid-state detectors, wherein the one or more solid-state detectors directly measure activity of the one or more radiation sources by capturing one or more images based on emissions received from the one or more radiation sources through the one or more plates.

2. The dose calibrator of claim 1 wherein dimensions of the dose calibrator comprise a height between 10 cm to 50 cm, a width between 10 cm to 50 cm and a depth between 10 cm to 50 cm.

3. The dose calibrator of claim 1 wherein the one or more solid-state detectors capture the one or more images based on the emissions at energies between 100 keV and 3 MeV.

4. The dose calibrator of claim 1 wherein the one or more solid-state detectors capture the one or more images based on the emissions at energies beyond 511 keV.

5. The dose calibrator of claim 1 wherein the one or more radiation sources are translatable along a first axis.

6. The dose calibrator of claim 1 wherein the one or more solid-state detectors are translatable along a second axis.

7. The dose calibrator of claim 1 wherein the one or more radiation sources are rotatable around one or more axes.

8. The dose calibrator of claim 1 wherein the one or more plates comprise one or more rotatable disks.

9. The dose calibrator of claim 1 wherein the one or more plates comprise one or more translatable plates.

10. The dose calibrator of claim 1 wherein the one or more plates comprise tungsten, lead or a combination thereof.

11. The dose calibrator of claim 1 wherein the one or more solid-state detectors comprise cadmium zinc telluride (CZT), cadmium telluride (CdTe), thallium bromide (TlBr) or combination thereof.

12. The dose calibrator of claim 1 wherein the one or more solid-state detectors comprise 1, 2 or 4 solid-state detectors.

13. A method of dose calibration comprising:
    positioning one or more radiation sources in a dose calibrator having one or more solid-state detectors;
    capturing, by the one or more solid-state detectors, one or more images based on emissions received from the one or more radiation sources through one or more plates between the one or more radiation sources and the one or more solid-state detectors in the dose calibrator; and
    directly measuring activity of the one or more radiation sources from the one or more images.

14. The method of claim 13 wherein estimating the activity of the one or more radiation sources comprises estimating a broad range of activities varying from range through Ci range.

15. The method of claim 13 further comprising adaptively adjusting one or more system parameters of the dose calibrator.

16. The method of claim 15 wherein adaptively adjusting the one or more system parameters comprises rotating or translating the one or more plates to adjust sizes or number of pinholes.

17. The method of claim 15 wherein adaptively adjusting the one or more system parameters comprises adaptively adjusting the one or more system parameters based on a measured dead-time.

18. The method of claim 15 wherein adaptively adjusting the one or more system parameters comprises adjusting distance between the one or more radiation sources and the one or more plates.

19. The method of claim 15 wherein adaptively adjusting the one or more system parameters comprises adjusting distance between the one or more solid-state detectors and the one or more plates.

20. A dose calibration system, comprising:
    one or more solid-state detectors;
    one or more plates positioned between one or more radiation sources and the one or more solid-state detectors, wherein the one or more solid-state detectors capture one or more images based on emissions received from the one or more radiation sources through the one or more plates; and
    a computer system communicatively coupled to the one or more solid-state detectors and the one or more plates, the computer system including a non-transitory memory device for storing computer readable program code, and a processor device in communication with the memory device, the processor being operative with the computer readable program code to perform steps including directly measuring activity of the one or more radiation sources from the one or more images.

* * * * *